US008524655B2

(12) United States Patent
Zhao et al.

(10) Patent No.: US 8,524,655 B2
(45) Date of Patent: Sep. 3, 2013

(54) USE OF SCF AND G-CSF IN THE TREATMENT OF CEREBRAL ISCHEMIA AND NEUROLOGICAL DISORDERS

(75) Inventors: Li-Ru Zhao, Shreveport, LA (US); John Kessler, Chicago, IL (US); Seema Singhal, Chicago, IL (US); Jayesh Mehta, Evanston, IL (US)

(73) Assignee: Northwestern University, Evanston, IL (US)

( * ) Notice: Subject to any disclaimer, the term of this patent is extended or adjusted under 35 U.S.C. 154(b) by 542 days.

(21) Appl. No.: 12/714,068

(22) Filed: Feb. 26, 2010

(65) Prior Publication Data
US 2010/0286039 A1  Nov. 11, 2010

Related U.S. Application Data

(63) Continuation of application No. 11/267,820, filed on Nov. 4, 2005, now abandoned.

(60) Provisional application No. 60/625,189, filed on Nov. 5, 2004.

(51) Int. Cl.
*A61K 38/00* (2006.01)
*A61K 38/18* (2006.01)

(52) U.S. Cl.
USPC ........ 514/1.1; 514/13.5; 514/17.7; 424/145.1

(58) Field of Classification Search
None
See application file for complete search history.

(56) References Cited

U.S. PATENT DOCUMENTS

| | | | |
|---|---|---|---|
| 4,810,643 A | 3/1989 | Souza | |
| 4,904,584 A | 2/1990 | Shaw | |
| 5,104,651 A | 4/1992 | Boone et al. | |
| 5,214,132 A | 5/1993 | Kuga et al. | |
| 5,218,092 A | 6/1993 | Sasaki et al. | |
| 5,362,853 A | 11/1994 | Kuga et al. | |
| 5,606,024 A | 2/1997 | Boone et al. | |
| 5,824,778 A | 10/1998 | Ishikawa et al. | |
| 5,824,784 A | 10/1998 | Kinstler et al. | |
| 6,017,876 A | 1/2000 | Gegg et al. | |
| 6,166,183 A | 12/2000 | Ishikawa et al. | |
| 6,204,363 B1 | 3/2001 | Zsebo et al. | |
| 6,207,417 B1 | 3/2001 | Zsebo et al. | |
| 6,207,454 B1 | 3/2001 | Zsebo et al. | |
| 6,207,802 B1 | 3/2001 | Zsebo et al. | |
| 6,218,148 B1 | 4/2001 | Zsebo et al. | |
| 6,248,319 B1 | 6/2001 | Zsebo et al. | |
| 6,261,550 B1 | 7/2001 | Osslund | |
| 2003/0064922 A1 | 4/2003 | Nissen et al. | |
| 2004/0141946 A1 | 7/2004 | Schacbitz et al. | |
| 2006/0246036 A1 | 11/2006 | Francis et al. | 424/93.2 |

FOREIGN PATENT DOCUMENTS

| | | |
|---|---|---|
| AU | A-76380/91 | 11/1991 |
| AU | A-10948/92 | 8/1992 |
| DE | 100 33 219 A1 | 1/2002 |
| EP | 0 243153 | 10/1987 |
| EP | 0 256843 | 2/1988 |
| EP | 0 272703 | 6/1988 |
| EP | 0 335423 | 10/1989 |
| EP | 0 370205 | 5/1990 |
| EP | 0 401384 | 12/1990 |
| EP | 0 456200 | 11/1991 |
| EP | 0 459630 | 12/1991 |
| EP | 0 473268 | 3/1992 |
| JP | 04164098 | 6/1992 |
| WO | WO 83/04053 | 11/1983 |
| WO | WO 89/05824 | 6/1989 |
| WO | WO 89/10932 | 11/1989 |
| WO | WO 90/06952 | 6/1990 |
| WO | WO 90/12874 | 11/1990 |
| WO | WO 91/02874 | 3/1991 |
| WO | WO 91/05795 | 5/1991 |
| WO | WO 91/05798 | 5/1991 |
| WO | WO 91/11520 | 8/1991 |
| WO | WO 91/18911 | 12/1991 |
| WO | WO 92/00376 | 1/1992 |
| WO | WO 92/03459 | 3/1992 |
| WO | WO 92/04455 | 3/1992 |
| WO | WO 92/06116 | 4/1992 |
| WO | WO 93/05169 | 3/1993 |
| WO | WO 93/15211 | 8/1993 |
| WO | WO 94/20069 | 9/1994 |
| WO | WO 95/21629 | 8/1995 |
| WO | WO 95/26199 | 10/1995 |
| WO | WO 96/11953 | 4/1996 |
| WO | WO 99/17798 | 4/1999 |

(Continued)

OTHER PUBLICATIONS

Petty et al. (Brain Res Rev 36: 23-34, 2001).*

(Continued)

*Primary Examiner* — Daniel E Kolker
*Assistant Examiner* — Aditi Dutt
(74) *Attorney, Agent, or Firm* — Marshall, Gerstein & Borun LLP

(57) ABSTRACT

The present invention relates to the use of stem cell factor (SCF) polypeptide, alone and in combination with granulocyte colony stimulating factor (G-CSF) polypeptide, in the prevention or treatment of injury to the brain after cerebral ischemia or neurological disorder. More particularly, the invention provides methods of improving neurological function and outcome after stroke by the administration of SCF polypeptide, alone and in combination with G-CSF polypeptide. This treatment can be used alone or in combination with other well-known methods of treatment of cerebral ischemia and neurological disorders in a mammal.

5 Claims, No Drawings

(56) References Cited

FOREIGN PATENT DOCUMENTS

| | | |
|---|---|---|
| WO | WO 01/51510 | 7/2001 |
| WO | WO 03/006501 | 1/2003 |
| WO | WO 03/030821 | 4/2003 |
| WO | WO 03/069310 A2 | 8/2003 |

OTHER PUBLICATIONS

Ashman, "The biology of stem cell factor and its receptor C-kit," *Int. J. Bioch. & Cell Biol.* 31:1037-1051, 1999.

Brazelton et al., "From marrow to brain: Expression of neuronal phenotypes in adult mice," *Science* 290:1775-1779, 2000.

Corti et al., "Modulated generation of neuronal cells from bone marrow by expansion and mobilization of circulating stem cells with in vivo cytokine treatment," *Exp. Neurol.* 177:443-452, 2002.

De Ryck et al., "Neocortical localization of tactile/proprioceptive limb placing reactions in the rat," *Brain Res.* 573:44-60, 1992.

Duan et al., "Sequential intrastriatal grafting of allogeneic embryonic dopamine-rich neuronal tissue in adult rats: Will the second graft be rejected?" *Neuroscience* 57:261-274, 1993.

Ferrari et al., "Muscle regeneration by bone marrow-derived myogenic progenitors," *Science* 279:1528-1530, 1998.

Fukunaga et al., "Growth and differentiation signals mediated by different regions in the cytoplasmic domain of granulocyte colony-stimulating factor receptor," *Cell* 74:1079-1087, 1993.

Gabrilove, "Introduction and overview of hematopoietic growth factors," *Semin. Hematol.* 26:2 (Suppl 2):1-4, 1989.

Görgen et al., "Granulocyte colony-stimulating factor treatment protects rodents against lipopolysaccharide-induced toxicity via suppression of systemic tumor necrosis factor-α," *J.Immunol.* 149:918-924, 1992.

Grabowski et al., "Paw-reaching, sensorimotor, and rotational behavior after brain infarction in rats," *Stroke* 24:889-895, 1993.

Hernandez et al., "Seizures and recovery from experimental brain damage," *Exp Neurol.* 102:318-324, 1988.

Hess et al., "Bone marrow as a source of endothelial cells and NeuN-expressing cells after stroke," *Stroke* 33:1362-1368, 2002.

Hesselink, "Stroke and Cerebral Ischemia," http://fmri.ucsd.edu/NeuroWeb/Text/br-710.htm#anchor208953.

Hirata et al., "Stem cell factor induces outgrowth of c-*kit*-positive neuritis and supports the survival of c-*kit*-positive neurons in dorsal root ganglia of mouse embryos," *Development* 119:49-56, 1993.

Hirata et al., "Characterization of c-*kit*-positive neurons in the dorsal root ganglion of mouse," *Develop. Brain Res.* 85:201-211, 1995.

Hirota et al., "Localization of mRNA for c-*kit* receptor and its ligand in the brain of adult rats: an analysis using in situ hybridization histochemistry," *Mol. Brain Res.* 15:47-54,1992.

Jackson et al., "Regeneration of ischemic cardiac muscle and vascular endothelium by adult stem cells," *J. Clin. Invest.* 107:1395-1402, 2001.

Jin et al., "Stem cell factor stimulates neurogenesis in vitro and in vivo," *J. Clin. Invest.* 110:311-319, 2002.

Jones et al., "Growth factors in haemopoiesis," *Bailliere's Clin. Hematol.* 2:83-111, 1989.

Katafuchi et al., "Impairment of spatial learning and hippocampal synaptic potentiation of c-kit mutant rats," *Learn. Mem.* 7:383-392, 2000.

Kawamata et al., "Intracisternal basic fibroblast growth factor (bFGF) enhances behavioral recovery following focal cerebral infarction in the rat," *J. Cereb. Blood Flow Metab.* 16:542-547, 1996.

Kocher et al., "Neovascularization of ischemic myocardium by human bone-marrow-derived angioblasts prevents cardiomyocyte apoptosis, reduces remodeling and improves cardiac function," *Nature Med.* 7:430-436, 2001.

Kuga et al., "Mutagenesis of human granulocyte colony stimulating factor," *Biochem. Biophys. Res. Comm.* 159:103-111, 1989.

Langley et al., "Properties of variant forms of human stem cell factor recombinantly expressed in *Escherichia coli*," *Arch. Biochem. Biophys.* 311:55-61, 1994.

Li et al., "Adult bone marrow transplantation after stroke in adult rats," *Cell Transplant* 10:31-40, 2001.

Lu et al., "Disulfide and secondary structures of recombinant human granulocyte colony stimulating factor," *Arch. Biochem. Biophys.* 268:81-92, 1989.

Lu et al., "Spontaneous dissociation-association of monomers of the human-stem-cell-factor dimer," *Biochem. J.* 305: 563-568,1995.

Manova et al., "c-*kit* receptor and ligand expression in postnatal development of the mouse cerebellum suggests a function for c-*kit* in inhibitory interneurons," *J. Neurosci.* 12:4663-4676, 1992.

Martin et al., "Primary structure and functional expression of rat and human stem cell factor DNAs," *Cell* 63:203-211, 1990.

Mezey et al., "Turning blood into brain: Cells bearing neuronal antigens generated in vivo from bone marrow," *Science* 290:1779-1782, 2000.

Moore et al., Synergy of interleukin 1 and granulocyte colony-stimulating factor: In vivo stimulation of stem-cell recovery and hematopoietic regeneration following 5-fluorouracil treatment of mice, *Proc. Natl. Acad. Aci. USA* 84:7134-7138, 1987.

Morstyn and Dexter, (eds.), "Filgrastim (r-metHuG-CSF) in Clinical Practice," Marcel Dekker, Inc., New York (1993), p. 351.

Motro et al., "Steel mutant mice are deficient in hippocampal learning but not long-term potentiation," *Proc. Natl. Acad. Sci. USA* 93:1808-1813, 1996.

Ohlsson et al., "Environment influences functional outcome of cerebral infarction in rats," *Stroke* 26:644-649, 1995.

Orlic et al., "Bone marrow cells regenerate infarcted myocardium," *Nature* 410:701-705, 2001.

Orlic et al., "Mobilized bone marrow cells repair the infarcted heart, improving function and survival," *Proc. Natl. Acad. Sci. USA* 98:10344-10349, 2001.

Orlic et al., "Adult bone marrow stem cells regenerate myocardium in ischemic heart disease," *Ann. N.Y. Acad. Sci.* 996:152-157, 2003.

Schäbitz et al., "Neuroprotective effect of granulocyte colony-stimulating factor after focal cerebral ischemia," *Stroke* 34:745-751, 2003.

Six et al., "Beneficial effect of pharmacological mobilization of bone marrow in experimental cerebral ischemia," *Eur. J. Pharmacol.* 458:327-328, 2003.

Souza et al., "Recombinant human granulocyte colony-stimulating factor: Effects on normal and leukemic myeloid cells," *Science* 232:61-65, 1986.

Spangrude et al., "Purification and characterization of mouse hematopoietic stem cells," *Science* 241:58-62, 1988.

Takano et al., "Pleiotropic effects of cytokines on acute myocardial infarction: G-CSF as a novel therapy for acute myocardial infarction," *Curr. Pharm. Des.* 9:1121-1127, 2003.

Weimann et al., "Contribution of transplanted bone marrow cells to Purkinje neurons in human adult brains," *Proc. Natl. Acad. Sci. USA* 100:2088-2093, 2003.

Welte et al., "Purification and biochemical characterization of human pluripotent hematopoietic colony-stimulating factor," *Proc. Natl. Acad. Sci. USA* 82:1526-1530, 1985.

Witte, "Steel locus defines new multipotent growth factor," *Cell* 63:5-6, 1990.

Zhang et al., "Cellular localization of stem cell factor and c-kit receptor in the mouse nervous system," *J. Neurosci. Res.* 47:1-15, 1997.

Zhao et al., "Human bone marrow stem cells exhibit neural phenotypes and ameliorate neurological deficits after grafting into the ischemic brain of rats," *Exp. Neurol.* 174:11-20, 2002.

International Search Report for PCT/US2005/039792.

Wang et al., "G-CSF/SCF treatments promote functional and structural recovery in ischemic rat brain," *Biosis|Bioscience Information Service*, XP002383300; Database accession No. PREV200400194514, 2003.

Zhao et al., "Brain repair by hematopoietic growth factors in a rat model of stroke," *Stroke* 38:2584-2591 (2007).

Zhao et al., "Hematopoietic growth factor pass through the blood-brain barrier in intact rats," *Exp. Neurol.* 204:569-573 (2007).

Zhao et al., "Beneficial effects of hematopoietic growth factor therapy in chronic ischemic stroke in rats," *Stroke* (2007).

Snyder and Olanow Curr Opin Neurol 18: 376-385, 2005.

Halliday et al Clin Exp Pharmacol Physiol 27: 1-8, 2000.

Steece-Collier et al., PNAS USA 99(22): 13972-13974, 2002.

Feigin et al., Curr Opin Neurol 15: 483-489, 2002.

Schneider et al., Cell cycle 12: 1753-1757, 2005.
Gerlach et al., J Neurol 249: III/33-III/35, 2002.
Katrin et al., J Neurochem 97: 675-686, 2006.
Cao et al. J Neurochem 99: 861-867, 2006.

Shyu et al., Circulaton 110: 1847-1854, 2004.
Sun et al. J Clin Invest 111: 1843-1851, 2003.

* cited by examiner

USE OF SCF AND G-CSF IN THE TREATMENT OF CEREBRAL ISCHEMIA AND NEUROLOGICAL DISORDERS

RELATED APPLICATIONS

This application is a continuation application of U.S. patent application Ser. No. 11/267,820, which was filed Nov. 4, 2005, now abandoned, which in turn claims benefit under 35 U.S.C. §119 of U.S. Provisional Patent Application Ser. No. 60/625,189, which was filed Nov. 5, 2004, each of which is incorporated herein by reference in its entirety.

FIELD OF THE INVENTION

The present invention relates to the use of stem cell factor (SCF) polypeptide, alone and in combination with granulocyte colony stimulating factor (G-CSF) polypeptide, to prevent or repair injury to the brain resulting from cerebral ischemia and neurological disorders. More particularly, the invention provides methods of treating stroke by the administration of SCF polypeptide, alone and in combination with G-CSF polypeptide, to improve functional recovery in both acute and chronic stages of stroke.

BACKGROUND OF THE INVENTION

Stroke is the leading cause of adult disability and the third cause of death worldwide. In the United States alone, a person has a stroke every 45 seconds, which accounts for approximately 700,000 people per year. Stroke is the third leading cause of death in the U.S., and it can lead to severe, long-term disability. In fact, more than two-thirds of stroke survivors are left with significant sensorimotor impairment. Stroke is a type of cardiovascular disease, which affects the arteries leading to and within the brain. When a stroke occurs, part of the brain starts to die from lack of blood flow and the part of the body it controls is affected. Damage to the brain can cause loss of speech, vision, or movement in an arm or a leg, depending on the part of the brain that is affected. Treatments are available to minimize the potentially devastating effects of stroke, but to receive them one must recognize the warning signs and act quickly.

A stroke occurs when a blood vessel that carries oxygen and nutrients to the brain is either blocked by a clot or bursts. Clots that block an artery cause ischemic strokes, which account for about 70-80 percent of all strokes. Cerebral ischemia induced by stroke leads to rapid death of neurons and vascular structures in the supplied region of the brain. The loss of neurons, arterioles, and capillaries in the infarcted zone is irreversible and results in the formation of scar tissue over time. For this reason, most experimental and clinical therapies have mainly focused on limiting infarct size. Attempts to replace the necrotic zone of the brain by transplanting fetal brain cells and other stems cells have been done, and although these attempts have been successful in the survival of many of the grafted cells, they have invariably failed to reconstitute healthy neurons and cerebral vessels integrated structurally and functionally with the spared cerebral tissue.

Recently, bone marrow stem cells (BMSC) have been shown to have the capacity to colonize various tissues, proliferate, and differentiate into cell lineages of the host organ. BMSC have also been shown to be able to differentiate into neuronal cells (Mezey et al., *Science* 290:1779-1782, 2000). Moreover, brain injury has been shown to be sensed by distant stem cells with BMSC migration to the injured area of the brain and subsequent differentiation (Brazelton et al., *Science* 290:1775, 2000). Brazelton et al. (supra) showed the generation of neuronal phenotypes in the adult brain of mice after an adult bone marrow transplant; hundreds of marrow-derived cells in brain sections expressed gene products typical of neurons. Weimann et al. (*Proc. Natl. Acad. Sci. USA* 100: 2088-2093, 2003) confirmed that BMSC could cross the blood-brain barrier and contribute to the neurons in the brain by their study of male sex chromosomes in Purkinje neurons in the brain of female patients at autopsy who had received bone marrow transplants from male donors. Hess et al. (*Stroke* 33:1362-1368, 2002) also showed that BMSC incorporated into the vasculature in the ischemic zone after middle cerebral artery occlusion (MCAO) and expressed an endothelial cell and neuronal cell markers. Adult whole bone marrow, prelabeled with bromodeoxyuridine (BrdU), was transplanted into the ischemic boundary zone of the adult rat brain after MCAO and later expressed neuronal and astrocytic proteins, suggesting that intracerebral transplantation of bone marrow could potentially be used to induce plasticity in the ischemic brain (Li et al., *Cell Transplant* 10:31-40, 2001).

BMSC are known to be stimulated by various cytokines. Granulocyte colony stimulating factor (G-CSF) has been found to be useful, alone or in combination with stem cell factor (SCF), in the mobilization of BMSC. G-CSF and SCF have recently been used to increase the mobilization of BMSC into organs for tissue repair (Orlic et al., *Proc. Natl. Acad. Sci. USA* 98:10344-10349, 2001). The findings by Orlic et al. (supra) in a mouse model of acute myocardial infarction, induced by coronary artery ligation, suggested that the mobilization of primitive BMSC by these cytokines might offer a noninvasive therapeutic strategy for the regeneration of the myocardium lost as a result of acute myocardial infarction or other pathology. Other researchers have used G-CSF treatment after MCAO and demonstrated that this cytokine increases short-term survival and decreases infarct volume in mice four days after the ischemic event (Six et al., *Eur. J. Pharmacol.* 458:327-328, 2003). In another short-term study using the in vivo administration of G-CSF at the time of MCAO in rats, short-term survival rate increased and infarct volume decreased (Schabitz et al., *Stroke* 34:745-751, 2003). Schabitz et al. (supra) also showed that G-CSF had a neuroprotective effect on mouse cerebellar granule cells in culture. These studies suggest that G-CSF provides a protective effect to the brain after cerebral ischemia.

G-CSF causes an increase in the release of hematopoietic stem cells into the blood, and plays a role in the proliferation, differentiation, and survival of myeloid progenitor cells (Takano et al., *Curr. Pharm. Des.* 9:1121-1127, 2003). G-CSF is also useful, alone or in combination with other compounds, such as other cytokines, for growth or expansion of cells in culture (for example, for bone marrow transplants or ex vivo expansion).

It is evident that treatment with G-CSF shows promise in inducing BMSC to travel to the injured brain to minimize the potentially devastating effects of stroke. However, for this treatment to be effective, one must recognize the warning signs and act quickly. Thus, there is a need in the art to develop quick, easy, and effective treatments for cerebral ischemia. Accordingly, an object of the present invention is to provide such methods for the treatment of cerebral ischemia and other neurological disorders, which are discussed in further detail herein. The present invention provides the first functional studies demonstrating that treatment with SCF, alone and in combination with G-CSF, provides a regenerative, as well as protective, effect on neurological function after cerebral ischemia. The present invention also provides the first demonstration that this cytokine treatment actually improves neurological function after an ischemic event. Additionally, the present invention provides evidence that this cytokine treatment could restore impaired brain function even when administered during the chronic stage of stroke.

SUMMARY OF THE INVENTION

The present invention relates to stem cell factor (SCF) polypeptide and granulocyte colony stimulating factor (G-CSF) and uses thereof in the treatment of cerebral ischemia or neurological disorders. More specifically, the present invention provides methods of improving neurological function and outcome in a mammal suffering from cerebral ischemia or a neurological disorder. Such methods generally involve the recruitment of stem cells for neuronal development and neurological repair. SCF and G-CSF can also act directly on neurons and neural progenitor cells.

In one aspect, such a method generally would comprise administering an effective amount of a composition comprising SCF polypeptide, alone or in combination with G-CSF polypeptide. In one embodiment, the composition comprises SCF alone. In another aspect, such a method generally would comprise administering an effective amount of a composition comprising G-CSF polypeptide, alone or in combination with SCF polypeptide. In another embodiment, the composition comprises G-CSF alone. In a preferred embodiment, the composition comprises SCF polypeptide and G-CSF polypeptide together. In a further embodiment, the composition comprises at least one additional agent. Such additional agents would generally be selected from the group consisting of: a growth factor, thrombolytic agent, or neurotrophic factor, such as brain-derived neurotrophic factor (BDNF), nerve growth factor (NGF), glial cell line-derived neurotrophic factor (GDNF), basic fibroblastic growth factor (bFGF), epidermal growth factor (EGF), platelet-derived growth factor (PDGF), and insulin-like growth factor (IGF). In a further embodiment, the improvement in neurological function is characterized by improved motor skills and coordination. In yet another embodiment, the improvement in neurological function is characterized by improved brain plasticity. Still in further embodiments, the improvement in neurological function is characterized by increased neural progenitor cell proliferation and differentiation, increased neuronal cell signaling, increased neuronal survival, decreased neuronal apoptosis, decreased neuronal toxicity, decreased infarct volume, or decreased total tissue loss. In a preferred embodiment of the invention, the mammal is a human. In one embodiment the composition is administered during the chronic stage of stroke. In another embodiment, the composition is administered during the acute stage of stroke. In a further embodiment, the neurological disorder is selected from the group consisting of Alzheimer's Disease (AD), Parkinson's Disease (PD), Huntington's Disease (HD), motor neuron disease, amyotrophic lateral sclerosis (ALS), cerebral palsy, genetic syndromes, epilepsy, spinal cord injury, neurodevelopmental malformations, brain dysplasias, and other less common neurodegenerative disorders.

The invention further comprehends kits containing components for the treatment of cerebral ischemia and neurological disorders. Such a kit generally would comprise a composition comprising SCF polypeptide; a composition comprising G-CSF polypeptide; and, optionally, includes the use of at least one additional agent. The additional agent may be a growth factor, thrombolytic agent, or neurotrophic factor, such as brain-derived neurotrophic factor (BDNF), nerve growth factor (NGF), glial cell line-derived neurotrophic factor (GDNF), basic fibroblastic growth factor (bFGF), epidermal growth factor (EGF), platelet-derived growth factor (PDGF), and insulin-like growth factor (IGF).

The term "stem cell factor (SCF) polypeptide" or "SCF" as used herein refers to naturally-occurring SCF (e.g. natural human-SCF) as well as non-naturally occurring (i.e., different from naturally occurring) polypeptides having amino acid sequences and glycosylation sufficiently duplicative of that of naturally-occurring stem cell factor to allow possession of a hematopoietic biological activity of naturally-occurring stem cell factor. The term "SCF" as used herein is also defined as recombinantly produced SCF, or fragments, analogs, variants, or derivatives thereof as reported, for example in U.S. Pat. Nos. 6,204,363; 6,207,417; 6,207,454; 6,207,802; 6,218,148; and 6,248,319. Stem cell factor has the ability to stimulate growth of early hematopoietic progenitors which are capable of maturing to erythroid, megakaryocyte, granulocyte, lymphocyte, and macrophage cells. SCF treatment of mammals results in absolute increases in hematopoietic cells of both myeloid and lymphoid lineages. One of the hallmark characteristics of stem cells is their ability to differentiate into both myeloid and lymphoid cells (Spangrude, *Science* 241: 58-62, 1988).

The term "granulocyte colony stimulating factor (G-CSF) polypeptide" or "G-CSF" as used herein is defined as naturally-occurring human and heterologous species G-CSF, recombinantly produced G-CSF that is the expression product consisting of either 174 or 177 amino acids, or fragments, analogs, variants, or derivatives thereof as reported, for example in Kuga et al., *Biochem. Biophys. Res. Comm.* 159: 103-111, 1989; Lu et al., *Arch. Biochem. Biophys.* 268:81-92, 1989; U.S. Pat. Nos. 4,810,643; 4,904,584; 5,104,651; 5,214,132; 5,218,092; 5,362,853; 5,606,024; 5,824,778; 5,824,784; 6,017,876; 6,166,183; and 6,261,550; U.S. Pat. Appl. No. US 2003/0064922; EP 0 335423; EP 0 272703; EP 0 459630; EP 0 256843; EP 0 243153; WO 9102874; Australian Application document Nos. AU-A-10948/92 and AU-A-76380/91. Included are chemically modified G-CSFs, see, e.g., those reported in WO 9012874, EP 0 401384, and EP 0 335423. See also, WO 03006501; WO 03030821; WO 0151510; WO 9611953; WO 9521629; WO 9420069; WO 9315211; WO 9305169; JP 04164098; WO 9206116; WO 9204455; EP 0 473268; EP 0 456200; WO 9111520; WO 9105798; WO 9006952; WO 8910932; WO 8905824; WO 9118911; and EP 0 370205. Also encompassed herein are all forms of G-CSF, such as Albugranin™, Neulasta™, Neupogen®, and Granocyte®.

The term "cerebral ischemia" as used herein is defined as insufficient cerebral blood flow resulting in inadequate delivery of oxygen and glucose to the brain. As used herein, it is meant to be synonymous with stroke, which is the clinical syndrome of rapid onset of focal (or global or subarachnoid hemorrhage) cerebral deficit, with no apparent cause other than a vascular one.

The term "neurological disorder" as used herein refers to brain dysfunction and neurodegeneration resulting from such diseases or disorders, including, but not limited to, Alzheimer's Disease (AD), Parkinson's Disease (PD), Huntington's Disease (HD), motor neuron disease, amyotrophic lateral sclerosis (ALS), cerebral palsy, genetic syndromes, epilepsy, spinal cord injury, neurodevelopmental malformations, brain dysplasias, and other less common neurodegenerative disorders.

The term "neurological function" as used herein includes the multiple functions of the brain and nervous system including, but not limited to, fine and gross motor skills, vision and visual attention, hearing, memory, touch perception, emotional responses, consciousness, ability to respond to environment, judgment, language, word association, memory, ability to plan a sequence of complex movements needed to complete multi-stepped tasks, spontaneity in interacting with others, flexibility in thinking, persistence of a single thought, ability to focus on task, mood changes, social behavior, personality, problem solving, goal directed voluntary movements, integration of different senses that allows for understanding a single concept, ability to attend to more than one object at a time, ability to name an object, ability to locate the words for writing, ability to read, ability to draw, ability to distinguish left from right, ability to doing mathematics, awareness of body parts and/or surrounding space, eye and hand coordination, breathing, heart rate, swallowing, reflexes, blood pressure, digestion, temperature regulation and sweating, alertness, ability to sleep, sense of balance, and sleeping.

The term "brain plasticity" as used herein refers to an inherent capability of the brain to change functionally and structurally and to adjust in response to external stimuli and internal injury. Brain plasticity occurs throughout one's lifespan, and neuronal connections may be remodeled by experience. As used herein, brain plasticity includes neuronal or neural plasticity.

The term "brain cell differentiation" as used herein refers to the process whereby neuronal and neural progenitor cells exit the cell cycle and terminally differentiate into neurons, astrocytes, and oligodendrocytes.

The term "neuronal signaling" or "neurotransmission" as used herein refers to the process through which neurons communicate. During this process, an electrical impulse or an action potential (a temporary reversal of electrical charge across the membrane) is converted to a chemical signal in the form of a neurotransmitter. As a result of the movement of charged particles, a wave of electrical activity travels down the axon and results in depolarization. Neurotransmission occurs at the synapse and is initiated when the action potential arrives at the presynaptic neuron, causing a change in membrane potential. The altered membrane potential allows calcium ions to trigger the release of neurotransmitters into the presynaptic cleft. Neurotransmitters then bind to specific receptors on the postsynaptic neuron. Once an action potential has been transferred, neurotransmitters are either enzymatically broken down or recycled to engage in another cycle of neuronal signaling.

The term "neuronal apoptosis" as used herein refers to the process through which neurons undergo programmed cell death to dispose of damaged, unwanted, or unnecessary cells. Apoptosis is characterized by distinctive morphologic changes in the nucleus and cytoplasm, i.e., chromatin cleavage at regularly spaced sites and endonucleolytic cleavage of genomic DNA (DNA fragmentation) at internucleosomal sites.

The term "neuronal toxicity" as used herein refers to the state of being cytotoxic to neurons, resulting in neuronal degeneration.

The term "infarct volume" as used herein refers to the total volume of the lesion of the brain damaged by ischemia. Reduction in infarct volume is a standard measure of therapeutic success in animal stroke models. Infarct volume is measured by a variety of methods known to one of skill in the art. Some of these methods include magnetic resonance imaging (MRI) and measurements of serial sections of the brain.

The terms "effective amount" and "therapeutically effective amount" each refer to the amount of an SCF or G-CSF polypeptide, an SCF or G-CSF nucleic acid molecule, or an agent that induces SCF or G-CSF expression or SCF or G-CSF activity used to support an observable level of one or more biological activities of the SCF or G-CSF polypeptides set forth herein.

The terms "pharmaceutically acceptable carrier" or "physiologically acceptable carrier" as used herein refer to one or more formulation materials suitable for accomplishing or enhancing the delivery of the SCF or G-CSF polypeptide, or the SCF or G-CSF nucleic acid molecules as a pharmaceutical composition.

The term "thrombolytic agent" as used herein is meant to refer to any agent capable of either dissolving a fibrin-platelet clot, or inhibiting the formation of such a clot. Examples of thrombolytic agents include streptokinase, prourokinase, urokinase, and tissue-type plasminogen activator. Although natural t-PA may be employed, it is preferable to employ recombinant t-PA. The invention may additionally employ hybrids, physiologically active fragments or mutant forms of the above thrombolytic agents. The term "tissue-type plasminogen activator" as used herein is intended to include such hybrids, fragments and mutants, as well as both naturally-derived and recombinantly-derived tissue-type plasminogen activator. The invention further provides a method, wherein the thrombolytic or fibrinolytic agent is selected from the group consisting of streptokinase, urokinase, prourokinase, and tissue-type plasminogen activator. Additional tissue-type plasminogen activator variants such as alteplase, reteplase, and anistreplase are also contemplated. In a further embodiment, the invention provides methods wherein the composition includes the use of at least one additional agent. The additional agent may be a growth factor, thrombolytic agent, or neurotrophic factor, such as brain-derived neurotrophic factor (BDNF), nerve growth factor (NGF), glial cell line-derived neurotrophic factor (GDNF), basic fibroblastic growth factor (bFGF), epidermal growth factor (EGF), platelet-derived growth factor (PDGF), and insulin-like growth factor (IGF).

The term "acute stage of stroke" as used herein is meant to refer to the period of time, e.g., from immediately after stroke onset to 48 hours to several days after stroke onset when brain edema occurs and the blood-brain barrier is compromised due to brain ischemia.

The term "chronic stage of stroke" as used herein is meant to refer to the period of time that follows the acute stage of stroke.

DETAILED DESCRIPTION OF THE INVENTION

SCF has been found to be useful alone, or in combination with G-CSF, in the improvement of neurological function after cerebral ischemia. The present invention addresses a role for SCF polypeptide alone, or in combination with other agents such as, but not limited to, G-CSF in the treatment of cerebral ischemia and neurological disorders. More specifically, the invention contemplates methods for minimizing brain damage, increasing neural cell and glial cell regeneration, decreasing infarct volume and total tissue loss, and improving neurological function and patient outcome after a brain injury.

According to the invention, treatment with an effective amount of SCF polypeptide, alone and in combination with G-CSF polypeptide, in an animal model of human stroke improved neurological function as demonstrated by improved sensorimotor skills. These findings provide the first evidence of a functional study demonstrating that treatment with SCF, alone and in combination with G-CSF, can provide a possible protective, as well as possible regenerative, effect on neurological function after cerebral ischemia in both the acute and chronic stages of stroke.

Discussed in further detail herein below are methods of using SCF and G-CSF in the treatment of cerebral ischemia and neurological disorders; methods of administering SCF and G-CSF; pharmaceutical compositions comprising SCF and G-CSF; methods of using SCF and G-CSF to stimulate mobilization of bone marrow stem cells to promote neuronal repair and regeneration; an overview of cerebral ischemia, stroke, and stroke therapy insofar as it applies to the methods of the present invention; and sensorimotor tests used to measure improvement in neurological function after SCF and G-CSF treatment.

The section headings used herein are for organizational purposes only and are not to be construed as limiting the subject matter described therein. All references cited in this application are expressly incorporated by reference herein.

A. Use of Stem Cell Factor (SCF) in the Treatment of Cerebral Ischemia and Neurological Disorders The present section provides a description of the involvement of stem cell factor (SCF) in the improvement of neurological function after cerebral ischemia to the extent that such a description will facilitate a better understanding of the methods and compositions of the present invention.

In one embodiment, the methods of the present invention exploit the use of SCF polypeptide, alone and in combination with G-CSF polypeptide, for the improvement of neurological function in the brain to minimize damage or increase repair and regeneration in the brain after an ischemic event. It is also contemplated that SCF polypeptide can be used, alone and in combination with G-CSF polypeptide, to increase repair and regeneration in the brain to treat neurological disorders.

SCF, see PCT Pub. No. WO 91/05795; also called kit-ligand, PCT Pub. No. WO 92/03459, mast cell growth factor, see PCT Pub. WO 92/00376 and Steel factor (or "SF" or "SLF") (White, Cell 63:5-6, 1990) is hematopoietic factor which acts on hematopoietic and possibly neural progenitor cells. The gene encoding SCF has been cloned and expressed, e.g., Martin et al. (Cell 63:203-211, 1990), and PCT Pub. No. WO 91/05795, which is herein incorporated by reference in its entirety.

SCF is produced by bone marrow stromal cells and is expressed on both primitive and mature hematopoietic progenitor cells. SCFs having the ability to stimulate growth of primitive progenitors including early hematopoietic progenitor cells are contemplated herein for use in the methods of the invention. These SCFs also are able to stimulate non-hematopoietic stem cells such as neural stem cells and primordial germ stem cells. Such factors include purified naturally-occurring stem cell factors. The invention also relates to non-naturally-occurring polypeptides having amino acid sequences sufficiently duplicative of that of naturally-occurring stem cell factor to allow possession of a hematopoietic biological activity of naturally occurring stem cell factor. Within the human haemopoietic system, SCF receptor, c-Kit, is expressed by approximately 70% of CD34+ cells in bone marrow, as well as by megakaryocytes, mononuclear cells, and activated platelets (Ashman, Int. J. Bioch. & Cell Biol., 31:1037-1051, 1999). C-Kit activates signal transduction pathways common to many growth factor receptors.

In the adult mouse brain, SCF is produced by neurons whereas c-Kit is expressed in glial cells and in some population of neurons (Zhang and Fedoroff, J. Neurosci. Res. 47:1-15, 1997). Purkinje cells also express SCF, whereas c-Kit is expressed in basket, stellate, and Golgi cells that established synapses to the Purkinje cells (Manova et al., J Neurosci. 12:4663-4676, 1992). The synaptic connecting neurons expressing SCF and c-Kit are noted in the hippocampus as well (Hirota et al., Mol. Brain Res. 15:47-54.1992; Zhang and Fedoroff, supra). SCF mutant mice demonstrate a deficit in spatial learning and memory (Motro et al., Proc. Natl. Acad. Sci. USA 93:1808-1813, 1996), whereas c-Kit mutant mice demonstrate an impairment of long-term potentiation and (Katafuchi et al., Learn. Mem. 7:383-392, 2000).

One hallmark of SCF activity is expansion of primitive progenitor cells in the marrow and peripheral blood. SCF has numerous active forms, including a membrane bound version and a soluble version. See PCT Pub. No. 91/05795. C-terminal deletion analogs also have activity. For example, SCF 1-137 (with "1" referring to the first amino acid of the mature protein) demonstrates biological activity, and SCF 1-141 demonstrates more or less full biological activity (Langley et al., Arch. Biochem. Biophys. 311:55-61, 1994). SCF 1-165 having an aspartic acid at position 10, instead of an asparagine as in the native sequence (referred to as "N10D") has also been studied, and found to not appreciably influence the rate of dimer formation (Lu et al., Biochem. J. 305: 563-568, 1995). Certain covalently linked SCF dimers are reported in PCT publication WO 95/26199. Stability is reportedly increased by an intermolecular covalent linkages.

In addition to naturally-occurring allelic forms of SCF, the present invention also embraces other SCF products such as polypeptide analogs of SCF. Such analogs include fragments of SCF. According to the procedures of the published application by Alton et al. (WO 83/04053), one can readily design and manufacture genes coding for microbial expression of SCF polypeptides having primary conformations which differ from SCF specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of SCF. Such products share at least one of the biological properties of SCF but may differ in others. SCF as used in the invention includes those which are foreshortened by e.g., deletions; or those which are more stable to hydrolysis (and, therefore, may have more pronounced or longer-lasting effects than naturally-occurring); or which have been altered to delete or to add one or more potential sites for O-glycosylation and/or N-glycosylation or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells. SCF analogs with increased biological activity and stability, such as those provided herein, would be desirable for use in medical treatments, as lower dosages may be used to achieve the same biological result. Also comprehended are polypeptide fragments duplicating only a part of the continuous amino acid sequence or secondary conformations within SCF, which fragments may possess one property of SCF (e.g., early hematopoietic cell growth activity) and not others (e.g., receptor binding).

B. Use of Granulocyte Colony Stimulating Factor (G-CSF) in the Treatment of Cerebral Ischemia and Neurological Disorders In another embodiment, the methods of the present invention exploit the use of G-CSF polypeptide, alone and in combination with SCF polypeptide, for the improvement of neurological function in the brain to minimize damage or increase repair and regeneration in the brain after an ischemic event. It is also contemplated that G-CSF polypeptide can be used, alone and in combination with SCF polypeptide, to increase repair and regeneration in the brain to treat a neurological disorder. G-CSF polypeptide, alone and in combination with SCF polypeptide, has a role in the mobilization of BMSC to the brain to increase neuronal repair. G-CSF causes an increase in the release of hematopoietic stem cells into the blood, and plays a role in the proliferation, differentiation, and survival of myeloid progenitor cells (Takano et al., *Curr. Pharm. Des.* 9:1121-1127, 2003). G-CSF and other hematopoietic growth factors including interleukin-3 (IL-3), IL-6, granulocyte-macrophage colony stimulating factors (GM-CSF), and stem cell factor (SCF) have all been reported to be positive regulators of granulopoiesis, the production of granulocytes in the bone marrow (Takano et al., *Curr. Pharm. Des.* 9:1121-1127, 2003).

Some research reports have indicated that G-CSF mobilized bone marrow stems cells can promote myocardial repair. For example, Kocher et al. (*Nature Med.* 7:430-436, 2001) demonstrated that the intravenous injection of adult human bone-marrow-derived endothelial cell precursors, mobilized by treatment with G-CSF, into a rat model of myocardial ischemia induced neoangiogenesis in the infarcted zone; prevented cardiomyocyte apoptosis; reduced scar formation, and improved ventricular function. G-CSF also has been shown to specifically stimulate the proliferation and differentiation of neutrophilic precursor cells into mature neutrophils (Fukunaga et al., *Cell* 74:1079-1087, 1993), and is well known for its usefulness in the treatment of neutropenic states (Welte et al., *Proc. Natl. Acad. Sci. USA* 82:1526-1530, 1985; Souza et al., *Science* 232:61-65, 1986; Gabrilove, *Sem. Hematol.* 26:1-14, 1989). G-CSF increases the number of circulating granulocytes and has been reported to ameliorate infection in sepsis models. G-CSF administration also inhibits the release of tumor necrosis factor (TNF), a cytokine important to tissue injury during sepsis and rejection (Wendel et al., *J. Immunol.* 149:918-924, 1992).

Human G-CSF can be obtained and purified from a number of sources. Natural human G-CSF can be isolated from the supernatants of cultured human tumor cell lines. The development of recombinant DNA technology has enabled the production of commercial scale quantities of G-CSF in glycosylated form as a product of eukaryotic host cell expression, and of G-CSF in non-glycosylated form as a product of prokaryotic host cell expression. See, for example, U.S. Pat. No. 4,810,643 (Souza) incorporated herein by reference.

G-CSF is produced by fibroblasts, macrophages, T cells, trophoblasts, endothelial cells, and epithelial cells, and is the expression product of a single copy gene comprised of four exons and five introns located on chromosome seventeen. In humans, endogenous G-CSF is detectable in blood plasma (Jones et al., *Bailliere's Clin. Hematol.* 2:83-111, 1989). G-CSF is species cross-reactive, such that when human G-CSF is administered to another mammal such as a mouse, canine, or monkey, sustained neutrophil leukocytosis is elicited (Moore et al., *Proc. Natl. Acad. Sci. USA* 84:7134-7138, 1987).

C. Administration of SCF and G-CSF

As mentioned herein above, it is contemplated that methods of the present invention will use SCF polypeptide, alone and in combination with G-CSF polypeptide, or G-CSF polypeptide, alone and in combination with SCF, in the treatment of cerebral ischemia and neurological disorders. SCF and G-CSF have been found to be useful in the treatment of conditions, wherein the mobilization of stem cells will provide benefits. SCF or G-CSF is useful alone, and in combination with G-CSF or SCF, respectively, or in combination with other compounds, which may act as thrombolytic agents or act to expedite tissue repair. The present section provides a description of how SCF and G-CSF may be therapeutically administered in the methods of the invention.

One of the therapeutic embodiments of the present invention is the provision, to a subject in need thereof, compositions comprising SCF polypeptide, alone and in combination with G-CSF polypeptide. Another embodiment of the present invention is the provision, to a subject in need thereof, compositions comprising G-CSF polypeptide, alone and in combination with SCF polypeptide. SCF and/or G-CSF polypeptides may have been generated through recombinant means or by automated peptide synthesis. The SCF and/or G-CSF formulations for such a therapy may be selected based on the route of administration and may include liposome and micelle formulations as well as classic pharmaceutical preparations.

SCF and/or G-CSF proteins are formulated into appropriate preparation and administered to one or more sites within the subject in a therapeutically effective amount. In particularly preferred embodiments, the human SCF and/or G-CSF protein-based therapy is effected via continuous or intermittent intravenous administration. By "effective amount" the present invention refers to that amount of human SCF and/or G-CSF polypeptide that is sufficient to support an observable change in the level of one or more biological activities of SCF and/or G-CSF. The change may be an increased level of SCF and/or G-CSF activity. Preferably, the change is an increase in BMSC mobilization or circulation to the ischemic or damaged tissue resulting in diminished tissue damage or increased tissue growth.

Those of skill in the art will understand that the amounts of human SCF and/or G-CSF polypeptides administered for therapeutic use may vary. It is contemplated that the specific activity of the human SCF and/or G-CSF protein preparation may be in the range of about 100 units/mg of protein to about 500 units/mg protein. Thus, a given preparation of a human SCF and/or G-CSF protein may comprise about 100 units/mg protein, about 125 units/mg protein, about 150 units/mg protein, about 175 units/mg protein, about 200 units/mg protein, about 225 units/mg protein, about 250 units/mg protein, about 275 units/mg protein, about 300 units/mg protein, about 325 units/mg protein, about 350 units/mg protein, about 375 units/mg protein, about 400 units/mg protein, about 425 units/mg protein, about 450 units/mg protein, about 475 units/mg protein and about 500 units/mg protein. A particularly preferred range is from about 100 units/mg protein to about 200 units/mg protein; a more preferable range is between about 150 to about 200 units/mg protein. Preferably, the protein composition is substantially free of contaminating factors, contamination level of less than 0.02% (w/w). Human SCF and/or G-CSF compositions, suitable for injection into a patient, can be prepared, for example, by reconstitution with a pharmacologically acceptable diluent of a lyophilized sample comprising purified human SCF and/or G-CSF and stabilizing salts.

Administration of the compositions can be systemic or local, and may comprise a single site injection of a therapeutically-effective amount of the human SCF and/or G-CSF protein composition. Any route known to those of skill in the art for the administration of a therapeutic composition of the invention is contemplated including, for example, intravenous, intramuscular, subcutaneous or a catheter for long-term administration. Alternatively, it is contemplated that the therapeutic composition may be delivered to the patient at multiple sites. The multiple administrations may be rendered simultaneously or may be administered over a period of several hours. In certain cases, it may be beneficial to provide a continuous flow of the therapeutic composition. Additional therapy may be administered on a period basis, for example, daily, weekly, or monthly.

In addition to therapies based solely on the delivery of the human SCF and/or G-CSF, combination therapy is specifically contemplated. In the context of the present invention, it is contemplated that the human SCF and/or G-CSF therapy could be used similarly in combination with other agents such as, but not limited to, G-CSF and SCF, respectively, that may promote mobilization of BMSC to the circulation, bone marrow, brain, and other organs.

To achieve the appropriate therapeutic outcome, using the methods and compositions of the present invention, one would generally provide a composition comprising human SCF, alone and in combination with human G-CSF, and at least one additional therapeutic agent (third therapeutic agent). Likewise, one may generally provide a compositions comprising human G-CSF, alone, and in combination with human SCF, and at least one additional therapeutic agent (third therapeutic agent). In the present invention, it is contemplated that the third therapeutic agent may involve the administration or inclusion of at least one additional factor selected from the group consisting of: EPO, MGDF, GM-CSF, M-CSF, CSF-1, IL-1, IL-2, IL-3, IL-4, IL-5, IL-6, IL-7, IL-8, IL-9, IL-10, IL-11, IL-12, or other various interleukins, IGF-1, LIF, interferon (such as $\alpha$, $\beta$, gamma or consensus), neurotrophic factors (such as BDNF, NT-3, CTNF or noggin), other multi-potent growth factors (such as, to the extent these are demonstrated to be such multi-potent growth factors, flt-3/flk-2 ligand, stem cell proliferation factor, and totipotent stem cell factor), fibroblast growth factors (such as FGF), human growth hormone and analogs, fusion molecules, and other derivatives of the above. For example, G-CSF in combination with SCF has been found to mobilize peripheral blood progenitor cells in vivo. Ex vivo, for example, G-CSF in combination with SCF, IL-3 and IL-6 has been found useful for expansion of peripheral blood cells. Likewise, SCF and/or G-CSF will provide for similar uses.

The combination therapy compositions would be provided in a combined amount effective to produce the desired therapeutic outcome in the treatment of cerebral ischemia and neurological disorder. This process may involve contacting the cells with human SCF polypeptide and/or human G-CSF polypeptide and a third or fourth agent(s) or factor(s) at the same time. This may be achieved by administering a single composition or pharmacological formulation that includes both or more agents, or by administering two or more distinct compositions or formulations, at the same time, wherein one composition includes the human SCF and/or G-CSF therapeutic composition, alone and in combination with G-CSF and/or SCF, respectively, and the other includes the third or fourth therapeutic agents.

Alternatively, the human SCF, human G-CSF, or human SCF+human G-CSF, treatment may precede or follow the other agent treatment by intervals ranging from minutes to weeks. In embodiments where the additional therapeutic agent and the human SCF, human G-CSF, or human SCF+ human G-CSF, are administered separately, one would generally ensure that a significant period of time did not expire between the times of each delivery, such that the additional therapeutic agent and the human SCF, human G-CSF, or human SCF+human G-CSF, would still be able to exert an advantageously combined effect. In such instances, it is contemplated that one would administer both or more modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Systemic delivery of human SCF and/or human G-CSF expression constructs or proteins to patients may be a very efficient method for delivering a therapeutically effective gene to counteract the immediate clinical manifestations of a disease. Alternatively, local delivery of the human SCF and/or human G-CSF and/or the additional therapeutic agent may be appropriate in certain circumstances.

D. Pharmaceutical Compositions Comprising SCF and G-CSF

As mentioned herein above, the present invention also comprehends methods using pharmaceutical compositions comprising effective amounts of SCF polypeptide, alone and in combination with G-CSF polypeptide, or G-CSF, alone and in combination with SCF, together with pharmaceutically acceptable diluents, preservatives, solubilizers, emulsifiers, adjuvants and/or carriers useful in SCF therapy, alone and in combination with G-CSF or G-CSF therapy, alone and in combination with SCF. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes or micelles. Such compositions will influence the physical state, stability, rate of in vivo release, and rate of in vivo clearance of SCF and G-CSF. See, e.g., Remington's Pharmaceutical Sciences, 18th Ed. (1990) Mack Publishing Co., Easton, Pa., pages 1435-1712, which are herein incorporated by reference.

Derivatives of SCF and G-CSF are also comprehended herein. Such derivatives include molecules modified by one or more water soluble polymer molecules, such as polyethylene glycol, or by the addition of polyamino acids, including fusion proteins (procedures for which are well-known in the art). Such derivatization may occur singularly at the N- or C-terminus or there may be multiple sites of derivatization. Substitution of one or more amino acids with lysine may provide additional sites for derivatization. (See U.S. Pat. Nos.: 5,824,784 and 5,824,778, incorporated by reference herein).

SCF and G-CSF or derivatives thereof may be formulated for injection, or oral, nasal, pulmonary, topical, or other types of administration as one skilled in the art will recognize. The formulation may be liquid or may be solid, such as lyophilized, for reconstitution.

SCF and G-CSF or derivatives thereof are useful in the treatment of cerebral ischemia and neurological disorder. Thus, the present methods may be useful for the treatment of such conditions. Other conditions alleviated or modulated by the administration of G-CSF are typically those characterized by a reduced hematopoietic or immune function and more specifically, a reduced neutrophil count. Such conditions may be induced as a course of therapy for other purposes, such as chemotherapy or radiation therapy. Such conditions may result from infectious disease, such as bacterial, viral, fungal, or other infectious disease. For example, sepsis results from bacterial infection. Or, such condition may be hereditary or environmentally caused, such as severe chronic neutropenia or leukemias. Age may also play a factor, as in the geriatric setting; patients may have a reduced neutrophil count or reduced neutrophil mobilization. Some of such conditions are reviewed in Filgrastim (r-metHuG-CSF) In: Clinical Practice, Morstyn and Dexter (eds.), Marcel Dekker, Inc., New York (1993), p. 351. Other less-studied conditions which may be alleviated or modulated by the administration of the present analogs may include the reduction of lipids (or cholesterol) in the blood stream and certain cardiovascular conditions, as G-CSF may induce the production of plasminogen activators. In addition, the present G-CSF analog compositions may be used for mobilization of peripheral blood progenitor cells. Thus, in yet another aspect, the present invention involves a method for culturing BMSC or peripheral blood progenitor cells (PBPC) with G-CSF.

In order to prepare human SCF and G-CSF containing compositions for clinical use, it will be necessary to prepare the viral expression vectors, proteins, and nucleic acids as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the human SCF and G-CSF analog or an expression vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the vectors or cells of the present invention, its use in therapeutic compositions is contemplated. Supplementary active ingredients also can be incorporated into the compositions.

The active compositions used in the methods of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramuscular, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption (for example, aluminum monostearate and gelatin).

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients also can be incorporated into the compositions.

For oral administration of the compositions used in the methods of the present invention, SCF, alone and in combination with G-CSF, or G-CSF, alone and in combination with SCF, may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions used in the methods of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

Generally, effective amounts of SCF and G-CSF, or derivatives thereof, will be determined by the age, weight, and condition or severity of disease of the recipient. See, Remington's Pharmaceutical Sciences, supra, pages 697-773, herein incorporated by reference. Typically, a dosage of between about 0.001 µg/kg body weight/day to about 1000 µg/kg body weight/day, may be used, but more or less, as a skilled practitioner will recognize, may be used. A preferred dosage in an adult human is approximately 300 µg/day. Dosing may be one or more times daily, or less frequently, and may be in combination with other compositions as described herein. It should be noted that the present invention is not limited to the dosages recited herein.

"Unit dose" is defined as a discrete amount of a therapeutic composition dispersed in a suitable carrier. For example, where polypeptides are being administered parenterally, the polypeptide compositions are generally injected in doses ranging from 1 µg/kg to 100 mg/kg body weight/day, preferably at doses ranging from 0.1 mg/kg to about 50 mg/kg body weight/day. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, supra, pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

Appropriate dosages may be ascertained through the use of established assays for determining level of myocardial infarct in combination with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment.

It will be appreciated that the pharmaceutical compositions and treatment methods of the invention may be useful in fields of human medicine and veterinary medicine. Thus the subject to be treated may be a mammal, preferably a human.

In addition, the present invention contemplates a kit containing components for treating cerebral ischemia and other neurological disorders comprising a composition comprising SCF, alone or in combination with G-CSF, or G-CSF, alone or in combination with G-CSF, and optionally, at least one additional factor.

E. Methods of Using SCF and G-CSF to Stimulate Mobilization of Bone Marrow Stem Cells for Tissue Repair and Regeneration The methods of the present invention contemplate using SCF polypeptide, alone or in combination with G-CSF polypeptide, or G-CSF, alone or in combination with SCF, to stimulate the mobilization of BMSC to the brain to promote neuronal repair and tissue regeneration in the treatment of cerebral ischemia and neurological disorders. Therefore, the present section provides a brief summary of what is known about the role of BMSC in tissue regeneration to the extent that such a summary will facilitate a better understanding of the methods of the present invention.

Primitive cells in bone marrow have the capacity, both in vitro and in vivo, to give rise to cells of all three germ layers. Stem cells of mesenchymal/stromal and hematopoietic origin have been suggested to have the potential to differentiate like embryonic stem cells. However, the mechanism for this "transdifferentiation" of adult stem cells is controversial and not well understood (Orlic et al., *Ann. N.Y. Acad. Sci.* 996: 152-157, 2003).

BMSC replacement therapy is contemplated in the methods of the invention for tissue repair and regeneration. Tissue regeneration using BMSC is known in the art and has been demonstrated in a variety of tissues including, but not limited to, muscle (Ferrari et al., *Science* 279:1528-1530, 1998) and heart (Jackson et al., *J. Clin. Invest.* 107:1395-1402; Kocher et al., *Nature Med.* 7: 430-436, 2001; Orlic et al., *Nature* 410: 701-705, 2001; and Orlic et al., *Proc. Natl. Acad. Sci. USA* 98:10344-10349, 2001). Orlic et al. (*Nature* 410:701-705, 2001) used direct injection of bone marrow stem cells into the heart three to five hours after ligation of the left coronary artery in a mouse model, resulting in the generation of new cardiomyocytes and endothelial cells in the zone of ischemic myocardium. These same researchers later reported that the proliferation of bone marrow stem cells in mice, effected by the treatment of mice with G-CSF prior to affecting occlusion of the left coronary artery, could ameliorate myocardial injury induced by the occlusion (Orlic et al., *Proc. Natl. Acad. Sci. USA* 98:10344-10349, 2001). Taken together, these studies suggest that stem cell therapy provides a novel therapeutic strategy in regenerating tissue and treating ischemic disease.

The present invention contemplates the use of SCF, alone and in combination with G-CSF, or G-CSF, alone and in combination with SCF, to stimulate the mobilization of BMSC to promote neuroregeneration in the brain for the treatment of cerebral ischemia and neurological disorders. Therefore, the present section provides a brief summary of what is known about the role of SCF and/or G-CSF in the mobilization of BMSC to the extent that such a summary will facilitate a better understanding of the methods of the present invention.

The systemic injection of SCF and G-CSF dramatically increased bone marrow-derived neurons in the adult mouse brain (Corti et al., *Exp. Neurol.* 177:443-452, 2002). In fact, there has been substantial evidence to suggest that SCF and its receptor, c-Kit, are involved in neurogenesis and neuronal plasticity. Jin and colleagues (*J. Clin. Invest.* 110:311-319, 2002) reported that c-Kit is expressed in the subventricular zone (SVZ) and subgranular zone (SGZ), and that the intraventricular administration of SCF increased the number of BrdU-labeled cells in both SVZ and SGZ, resulting in enhanced neurogenesis. SCF also increased neurite outgrowth embryonic dorsal root ganglia whereas c-Kit was shown to be expressed in the growth cones (Hirata et al., *Development* 119:49-56, 1993; and Hirata et al., *Develop. Brain Res.* 85:201-211, 1995). Six and co-workers (*Eur. J. Pharmacol.* 458:327-328, 2003) reported that G-CSF reduced infarct volume when it was injected 24 h after brain ischemia. SOX1, a neuroprogenitor indicator, was markedly increased in SVZ and migrated into peri-infarction area three months after brain ischemia in rats (Zhao et al., unpublished data). However, no studies to date have investigated the therapeutic effect on the brain of the combination therapy of SCF+G-CSF administration at both the acute and the chronic stages of stroke.

F. Cerebral Ischemia, Stroke, and Stroke Therapy

As discussed throughout the specification, the present invention contemplates methods of using SCF polypeptide, alone and in combination with G-CSF polypeptide, or G-CSF, alone and in combination with SCF, for the treatment of cerebral ischemia and other neurological disorders. The present section provides an overview of the events that take place in cerebral ischemia and stroke to the extent that such a description will facilitate a better understanding of the methods of the present invention. Information regarding cerebral blood flow and pathologic changes in the brain after stroke have been described by John R. Hesselink, MD, FACR in an electronically posted text entitled IMAGING OF STROKE AND CEREBRAL ISCHEMIA on a University of California San Diego Neuroradiology website and were used in preparing a description of cerebral ischemia and stroke, as set out below.

The brain requires glucose and oxygen to maintain neuronal metabolism and function, which are carried to the brain via cerebral blood flow (CBF). Cerebral ischemia results from insufficient CBF. Normal human CBF is 50-55 ml/100 gm/min. If the CBF drops below 18, electrical activity ceases, and if the CBF dips below 12, neuronal metabolism stops. The consequences of cerebral ischemia depend on the degree and duration of reduced CBF. Neurons can tolerate ischemia for 30-60 minutes. Perfusion must be reestablished before 3-6 hours of ischemia have elapsed or before the CBF drops to 10. The range of CBF between 12 and 18 has been called the "ischemic penumbra" because the neuronal damage is mild and reversible if flow is restored within a few hours. Clinically, a window of opportunity is available to intervene therapeutically and to prevent the ischemic brain tissue from going on to infarction.

If CBF is not reestablished to the ischemic area, a series of metabolic processes ensue. Neurons become depleted of ATP and switch over to anaerobic glycolysis, lactate accumulates, and intracellular pH decreases. Without an adequate supply of ATP, the membrane ion pump fails. There is an influx of sodium, water, and calcium into the cell. The excess calcium is detrimental to cell function and contributes to membrane lysis. Cessation of mitochondrial function signals neuronal death. The astrocytes and oligodendroglia are slightly more resistant to ischemia, but their demise follows shortly if blood flow is not restored.

Pathologic changes within the neuropil follow the metabolic abnormalities. One of the first effects is cytotoxic edema that results from failure of the Na/K ion pump. Early on, this stage is still reversible; however, prolonged ischemia leads to cell death and coagulation necrosis. After 3-6 hours of ischemia, irreversible damage occurs to the capillary endothelium. The blood-brain barrier becomes dysfunctional and serum proteins and water leak into the interstitial space. Some reperfusion is required to produce vasogenic edema, which is maximal when residual CBF is between 5 and 10. There is also an influx of macrophages to clean up the dead tissues. Capillary proliferation begins near the end of the first week. The end result of cerebral infarction is an area of encephalomalacia with some surrounding gliosis. The amount of gliosis depends on the number of surviving astrocytes.

Surgery, drugs, hospital care and rehabilitation are all accepted stroke treatments. When the carotid artery in the neck is partially blocked by a fatty buildup, called plaque, surgery called carotid endarterectomy might be used to remove the accumulated plaque. Cerebral angioplasty is another technique in which balloons, stents and coils are used to treat some types of problems with the brain's blood vessels. Its widespread use depends on its safety and effectiveness. The clot-dissolving drug tissue plasminogen activator (tPA) may be used to treat strokes caused by blood clots, which cause about 80 percent of all strokes. tPA dissolves the clot and restores blood flow to the brain. tPA carries a risk of bleeding in the brain, but its benefits outweigh the risks when an experienced doctor uses it properly.

Not every stroke patient, particularly those having a hemorrhagic stroke, should be treated with tPA. That's why it's extremely important to determine the type of stroke very quickly. tPA is effective only if given promptly. For maximum benefit, the therapy must be started within three hours of the onset of stroke symptoms. That is why it is so critical that the stroke is recognized immediately as a medical emergency and treatment be given immediately.

Although known treatments may provide some relief to the damaged tissue and inhibit further scarring of the brain, the infarcted brain does not regenerate. Therefore, the present invention provides a novel method of using SCF polypeptide, alone and in combination with G-CSF polypeptide, to minimize brain damage, induce brain tissue regeneration, and improve neurological function after an ischemic event. The present invention even minimizes brain damage, induces brain tissue regeneration, and improves neurological function during the chronic stage of stroke, as demonstrated, e.g., 14 weeks after ischemic onset.

G. Sensorimotor Tests

The present section provides examples of some sensorimotor (behavioral) tests that are used in the art to measure motor function improvement after treatment using the methods of the invention. One of skill in the art will realize that there are numerous additional tests that can be used to measure improvements in sensorimotor function after treatment of cerebral ischemia and neurological disorders using the methods of the invention. Some known tests are provided below.

Limb Placement Tests

The limb placement test includes eight subtests (Ohlsson et al., *Stroke* 26:644-649, 1995; Zhao et al., *Exp. Neurol.* 174: 11-20, 2002). Briefly, the forelimbs of a rat are tested on a counter top surface and at its edges. For each subtest, an animal receives a score of 0 if it is unable to place its limbs, a score of 1 if there is a partial and/or delayed (more than 2 seconds) placement of its limbs, or a score of 2 if the animal exhibits an immediate and correct placement of its limbs. For each body side, the maximal score is 16. (0, severe neurological deficits; 16, no neurological deficits).

In another forelimb-placement test, animals are held gently by the torso, which allows their forelimbs to hang free, and are moved slowly toward a table top until the dorsal forepaw surface barely touches the edge. Normal animals rapidly place their forelimb on the table top. Depending on the extent of motor injury, placing of the forelimb contralateral to the injury in response to contralateral contact with the table top may be impaired. Performance is scored between 0 (normal) and 10 (maximal impairment) (Kawamata et al., *J. Cereb. Blood Flow Metab.* 16:542-547, 1996; De Ryck et al., *Brain Res.* 573:44-60, 1992). Similarly, the hindlimb-placing test evaluates the animal's ability to place the hindpaw on a table in response to light stimulation and is scored on a 0-6 scale.

Foot Fault Test

In a foot fault test, animals are placed on elevated hexagonal grids of 2 sizes to test placement dysfunction of the forepaw (Hernandez et al., *Exp Neurol.* 102:318-324, 1988). Grids have openings of either 3 cm (small) or 6 cm (large). Both grid sizes may be chosen to allow comparison with other studies that use either small or large grids. Rats place their paws on the wire while moving along the grid. Rats may then be videorecorded from below the grid for ease in recording the stepping pattern. With each weight-bearing step, the paw may fall or slip between the wires. This is recorded as a foot fault. The number of faults for the forepaw contralateral to the infarction is recorded along with the number of successful steps and displayed as a percentage of contralateral forelimb foot faults per forelimb steps. Faults are calculated for both sizes of grids. Baseline percentages are acquired by testing sham-operated rats or rats preoperatively (control).

Paw-Reaching Test

The paw-reaching test also provides a stable behavioral parameter after a middle cerebral artery occlusion (Grabowski et al., *Stroke* 24:889-895. 1993). Moreover, the lesion-induced deficit in paw-reaching is highly correlated to the extent of the infarct, suggesting that this test is useful in evaluating treatment effects over a longer period of time.

H. EXAMPLES

The present invention is described in more detail with reference to the following non-limiting examples, which are offered to more fully illustrate the invention, but are not to be construed as limiting the scope thereof. The examples illustrate the treatment of an animal model of stroke with SCF polypeptide and G-CSF polypeptide in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

SCF and G-CSF Administration Improves Neurological Function in a Limb Placement Test in a Rat Model of Stroke To determine whether treatment with the cytokines, SCF and G-CSF, alone or in combination, improves functional outcome after stroke, rats were subject to experimental stroke and examined for neurological function improvement after cytokine treatment post-stroke. Rats were subject to anesthesia (methohexital sodium, 50 mg/kg, intraperitoneally, Monarch Pharmaceuticals) and permanent ligation/occlusion of the right middle cerebral artery, distal to the striatal branch, and ligation of the ipsilateral common carotid artery. Three hours post-ischemia, rats were treated with SCF and G-CSF and subjected to a limb-placement test for the evaluation of neurological deficits.

After induction of cerebral ischemia, adult male spontaneously hypertensive rats (250-350 g) were randomly divided into four experimental groups as follows: 1) control (saline only; n=10); 2) SCF (n=10); 3) G-CSF (n=10); or 4) SCF+G-CSF (n=11). Sham-operated rats served as a group of intact controls. All treatments were initiated three hours after cerebral ischemia, and then were administered daily for seven days. Rat SCF (r SCF, 0.88 mg/ml) was administered at a dosage of 200 µg/kg subcutaneously daily and human G-CSF [rh G-CSF (filgrastim) 3.00 mg/ml] was administered at a dosage of 50 µg/kg subcutaneously daily for seven days.

Neurological deficits were evaluated using the limb-placement test (score 0=severe neurological deficits; score 16=no neurological deficits). The test was performed blindly before administration of the cytokines, and at one, four, seven, and ten weeks after the final injections of the cytokines. SCF treatment caused significant neurological functional improvement as early as one week after cytokine treatment when compared with control ($p<0.01$), G-CSF ($p<0.05$), and SCF+G-CSF ($p<0.05$) treatment groups. At four weeks post-cytokine treatment, both SCF as well as SCF+G-CSF treated groups displayed improved neurological function when compared to controls (SCF vs. control, $p<0.01$; SCF+G-CSF vs. control, $p<0.01$) or G-CSF treatment alone (SCF vs. G-CSF, $p<0.05$; SCF+G-CSF vs. G-CSF, $p<0.01$). Seven and ten weeks after cytokine administration, rats treated with SCF alone and SCF+G-CSF demonstrated significantly higher scores than controls or rats given G-CSF treatment alone (both=$p<0.01$). Rats treated with G-CSF alone showed better neurological performance than controls at both one and ten weeks ($p<0.05$) after cytokine administration. Data (means +/− SEM) were tested by Kruskal Wallis non-parametric analysis with post hoc multiple comparisons.

This example illustrates that treatment with SCF and G-CSF, alone or in combination, significantly improved sensorimotor function after experimental stroke. This example also reveals the first demonstration that treatment with SCF and G-CSF, alone or in combination, after stroke provides a novel and effective therapy for stroke patients.

Example 2

SCF and G-CSF Administration Improve Neurological Function in a Foot-Fault Test in a Rat Model of Stroke In another test to determine whether the administration of SCF and G-CSF, alone or in combination, at three hours after cerebral ischemia, improves functional outcome after stroke, ischemic rats were subjected to a foot-fault test and evaluated for improvements in neurological function.

As set out in Example 1, rats were randomly divided into the same four experimental groups and given the same treatments. Neurological deficits were evaluated using the foot-fault test (10 foot faults in 10 steps=severe neurological deficits; no foot faults=no neurological deficits). The test was performed blindly before administration of the aforementioned cytokines, and at one, four, seven, and ten weeks after the final injections of the cytokines. SCF treatment caused significant neurological functional improvement as early as one week after cytokine treatment when compared with control ($p<0.01$), G-CSF ($p<0.01$), and SCF+G-CSF ($p<0.01$) treatment groups. At four weeks post-cytokine treatment, both SCF as well as SCF+G-CSF treated groups displayed improved neurological function when compared to controls (SCF vs. control, p<0.01; SCF+G-CSF vs. control, p<0.01) or G-CSF treatment alone (SCF vs. G-CSF, p<0.05; SCF+G-CSF vs. G-CSF, p<0.01; SCF+G-CSF vs. SCF, p<0.01). SCF+G-CSF also showed improvement over SCF alone. Seven and ten weeks after cytokine administration, rats treated with SCF alone or SCF+G-CSF exhibited significantly fewer foot-faults than controls or rats given G-CSF treatment alone (both=p<0.01). Data (means +/− SEM) were analyzed by ANOVA with post hoc multiple comparisons.

This example illustrates that treatment with SCF and SCF+G-CSF significantly improved functional recovery after experimental stroke and provides further support that SCF and SCF+G-CSF treatment after stroke may provide an effective therapy for stroke patients.

Example 3

The Effect of SCF and G-CSF Administration on Body Weight

To determine whether treatment with SCF and G-CSF, alone or in combination, significantly affect body weight, rat body weights were measured before MCAO and at one, four, and seven weeks post-cytokine treatments.

As set out in Example 1, rats were randomly divided into the same four experimental groups and given the same treatments. Rats that received G-CSF alone showed a significant reduction in body weight at one week post-cytokine administration compared to all other groups (p<0.01). However, by four weeks post-treatment, the lost body weight was regained and there were no significant differences in body weight between any of the treatment groups throughout the remainder of the experiments. SCF and SCF+G-CSF treatments did not have any effect on body weight.

This example illustrates that treatment with G-CSF causes a transient reduction in body weight early after treatment, but no significant differences after prolonged therapy. Thus, SCF and SCF+G-CSF had no effect on body weight during cytokine therapy.

Example 4

SCF and G-CSF Improve Functional Recovery During the Chronic Stage of Stroke in Senior Animals To determine whether SCF and G-CSF, alone or in combination, can improve functional outcome of the brain in senior animals during ischemia at the chronic stage of stroke, 44 spontaneously hypertensive senior rats were subjected to focal brain ischemia and treated with the cytokines over three months post-ischemic event.

Fourteen weeks after brain ischemia, neurological deficit-matched animals were randomly divided into four treatment groups: phosphate-buffered saline (PBS) controls (n=11), SCF (n=11), G-CSF (n=11), and SCF+G-CSF (n=11). Rats received daily injections subcutaneously of SCF, G-CSF, SCF+G-CSF, or equal volume of PBS (control) for seven days. One week and five weeks after the injections of cytokines, neurological deficits were evaluated with limb placement test and foot fault test. Data showed significant functional improvement in the cytokine-treated animals. Rats that were injected with both SCF+G-CSF were superior to all other groups in the performance of the limb placement test and the foot fault test. (Limb placement test at one week: PBS vs. SCF+G-CSF, p<0.01; G-CSF vs. SCF+G-CSF, p<0.01; foot fault test at one week: PBS vs. SCF, p<0.05; PBS vs. SCF+G-CSF, p<0.01; SCF+G-CSF vs. G-CSF, p<0.01; SCF vs. G-CSF, p<0.05; limb placement test at five weeks: PBS vs. SCF+G-CSF, p<0.01; PBS vs. SCF, p<0.05; G-CSF vs. SCF+G-CSF, p<0.01; SCF vs. SCF+G-CSF, p<0.01; foot fault test at five weeks: SCF+G-CSF vs. PBS, p<0.01; SCF+G-CSF vs. G-CSF, p<0.01; limb placement test at 17 weeks: SCF+G-CSF vs. PBS, p<0.01; SCF+G-CSF vs. G-CSF, p<0.01; and foot fault test at 17 weeks: SCF+G-CSF vs. PBS, p<0.01; SCF+G-CSF vs. G-CSF, p<0.01). The data from the limb placement test were analyzed by a Kruskal-Wallis non-parametric analysis with post hoc multiple comparisons, and the data obtained from the foot fault tests were analyzed by a one-way ANOVA with post hoc multiple comparisons.

Consequently, this example provides evidence that the administration of SCF and G-CSF, alone or in combination, improved the functional outcome of the brain in senior animals, fourteen weeks after brain ischemia, at the chronic stage of stroke. Rats that received both SCF and G-CSF showed the most significant improvement in sensorimotor function.

Example 5

SCF and G-CSF Administration Improve Neurological Function in a Field Evoked Potential Study in a Rat Model of Stroke In another test to determine whether SCF and G-CSF, alone or in combination, improves functional outcome after stroke, rats were treated with SCF and G-CSF, alone or in combination, after ischemic surgery and subjected to a field evoked potential study. Neural activities in the intact and affected cortex were recorded by field evoked potential at 19 weeks after injection of cytokines (as set out in Example 4). A field evoked potential is an electrophysiological approach to test the function and entirety of somatosensory pathways. The purpose of this study was to determine whether SCF and G-CSF, alone or in combination, could re-establish somatosensory pathways that were damaged by focal brain ischemia, and also to confirm the functional outcome of limb placement and foot-fault tests.

Evoked potentials are electrical signals generated by the nervous system in response to sensory stimuli. Auditory, visual, and somatosensory stimuli are used commonly for clinical evoked-potential studies. Somatosensory evoked potentials consist of a series of waves that reflect sequential activation of neural structures along the somatosensory pathways following electrical stimulation of peripheral nerves. The evoked potential of sensory neurons in the brain is recorded by local field potentials (LFP).

To perform the study, rats were anesthetized with isoflurane (1~1.5%) and two recording electrodes were placed on the ipsilateral and the contralateral skull (A: 1.0 mm rostral to the bregma, 2.0 mm lateral to the middling; B: 3.0 mm caudal to the bregma, 1.5 mm lateral to the midline). A stimulation needle was inserted under the skin of a digit, and the parameters of the stimulation were: 2 Hz, 0.4 mA, 500 ms interval and 300 μs duration. The stimulation lasted for 5 min and was repeated twice.

When stimulating the intact forepaw (right), the field evoked potential was recorded at the contralateral hemisphere (left intact hemisphere). No signal was recorded at the ipsilateral hemisphere (right affected hemisphere). The field evoked potentials in the intact contralateral hemisphere in G-CSF-treated rats treated were more sensitive than in the other three groups. When the stimulation was performed at the affected forepaw (left), neuronal activities were quite different among the groups. In the PBS-control rats, field evoked potentials were captured at both the contralateral (affected) and the ipsilateral (intact) hemispheres. In contrast, SCF+G-CSF-treated rats showed prominent neuronal activities in the affected (contralateral to the stimulation) hemisphere. No obvious signals were captured at the intact (ipsilateral to the stimulation) hemisphere. SCF-treated rats also exhibited obvious field evoked potential in the affected hemisphere; however, the waves were much wider than in the rats injected with SCF+G-CSF. A low evoked activity was recorded in the intact side (ipsilateral to the stimulation) of SCF-treated rats, but it was much lower than in the PBS controls. In G-CSF-treated rats, however, both hemisphere activities were lower than others. The data from the field evoked potential study was correlated to the results of neurological deficit tests (r=0.38, p<0.05). The neurological behavioral data were analyzed with a Kruskal-Wallis nonparametric analysis. A Mann-Whitney nonparametric analysis was used for further determination of the difference between groups.

This example confirmed the functional data of earlier experiments and provides evidence (using a field evoked potential) that SCF+G-CSF-treated rats exhibited prominent neuronal activity in the damaged hemisphere, whereas the rats with less functional recovery showed neuronal activities in both hemispheres.

Example 6

Ability of SCF and G-CSF to Cross the Blood-Brain Barrier in Vivo

To determine whether SCF or G-CSF polypeptides cross the blood-brain barrier, an experiment is performed to detect the presence of radioactive cytokines (SCF and G-CSF) in the blood and parenchyma of the brain after intravenous radiolabeled cytokine administration.

After anesthesia, rats are cannulated and labeled cytokines ($^{125}$I-labeled SCF and G-CSF, MP Biomedicals/Radiochemical Division) are injected intravenously into the rats. The concentrations of iodinated cytokines are measured in both the blood and in the parenchyma of the brains from nine rats per cytokine group, measured at three different time points after injection. The concentrations of SCF, G-CSF, and SCF+G-CSF are measured 20 min. after injection (n=3), 30 min. after injection (n=3), and 60 min. after injection (n=3) in both the blood and in the parenchymas.

Briefly, after anesthesia, catheters are inserted into the femoral artery and vein of each animal. Labeled cytokines are injected through the vein, and blood samples are taken from the artery at selected time intervals for liquid scintillation counting. At the end of the experiment, anesthetized animals are decapitated and their brains are rapidly removed and frozen in powdered dry ice. Brain slices are exposed on SB5 film (Kodak, Rochester, N.Y.) for collecting the [$^{125}$I]-image. The [$^{125}$I]-SCF or [$^{125}$I]-G-CSF images are digitized with a video-based digitizing system at a resolution of 50 mm/pixel and aligned in computer memory. Radioactivity in the blood and radioactive images are analyzed for the ability of cytokines to cross the blood-brain barrier.

Example 7

SCF and G-CSF Administration Decreased Brain Infarct Volume and Total Tissue Loss in a Rat Model of Stroke To determine whether SCF and G-CSF, alone or in combination, can decrease brain infarct volume and total tissue loss in senior animals after ischemia and cytokine therapy at the chronic stage of stroke, the following study was performed.

At 20 weeks post-cytokine treatment (as set out in Example 4), rats were anesthetized with pentobarbital sodium (50 mg/kg, i.p.) and transcardially perfused with 4% paraformaldehyde in 0.1M-phosphate buffer. Brains were cut into nine pieces, 2 mm thickness, with a brain matrix. Sections were photocopied and infarction volume was measured (Zhao et al., Exp. Neurol. 174:11-20, 2002) using a software package (Scion Image, Version Beta 4.0.2, Scion Corporation, Frederick, Md.). Considering the secondary damage, the infarction volume was presented as percentage of the contralateral hemisphere.

SCF+G-CSF-treated rats exhibited a significant decrease in both total tissue loss and infarction volume (percentage of the contralateral hemisphere) when compared to PBS controls (SCF+G-CSF vs. PBS: 307±164 vs. 555±205 mm$^3$, p=0.022; 9±6 vs. 16±6%, p=0.032) and G-CSF-treated rats (SCF+G-CSF vs. G-CSF: 307±164 vs. 506±107 mm$^3$, p=0.017; 9±6 vs 14±3%, p=0.015). In comparison to SCF-treated animals, total tissue loss was significantly decreased in SCF+G-CSF-treated rats (SCF+G-CSF vs SCF: 307±164 vs 620±239 mm$^3$, p=0.01).

Infarction volume was tested with a Kruskal-Wallis nonparametric analysis. A Mann-Whitney nonparametric analysis was used for further determination of the difference between groups. The difference in total tissue loss (mm$^3$) was examined with one way-ANOVA with Scheffé's post hoc determination. P<0.05 was considered for significant difference. Data were presented as mean±SD.

This example provides evidence that SCF+G-CSF treatment after stroke reduces total tissue loss and infarction volume (percentage of the contralateral hemisphere) when compared to PBS controls.

Example 8

Neuroprotective Effect(s) of SCF and G-CSF on Cortical Neurons In Vivo

Cortical brain ischemia induces a secondary cell loss in the ipsilateral thalamus due to loss of neuronal connections between thalamus and cortex. Thus, to determine if SCF and G-CSF, alone or in combination, can protect cortical neurons against secondary damage, experiments were performed to analyze the size of the ipsilateral thalamus after cortical brain ischemia. A series of coronal sections were taken from the thalamus and measured through the use of computer software (Scion Image). SCF and G-CSF, alone or in combination, administered 3 h after cerebral ischemia, did not reduce cortical brain ischemia in preliminary experiments. However, SCF receptor, c-Kit, was expressed in the border zone of the infarction, indicating that SCF may have a role in preventing apoptosis.

To further determine whether SCF and G-CSF, alone or in combination, plays a role in protecting neurons from apoptosis post-ischemia, animals are randomly divided into four groups and are administered the following treatments after induction of cortical brain ischemia by MCAO: SCF, G-CSF, SCF+G-CSF, and saline control. The cytokines and saline control are administered to rats via subcutaneous injection at the following dosages (SCF: 200 µg/kg; G-CSF: 50 µg/kg; and SCF: 200 µg/kg+G-CSF: 50 µg/kg) at 3 hours after brain ischemia. Rats (n=2 or 3) are sacrificed at 3 h, 6 h, 24 h, 3 d, and 7 d after brain ischemia. Brain sections are processed for immunohistochemistry to detect cells immunopositive for c-Kit, NeuN (neuronal marker), GFAP, and S-100 (astrocyte markers). TUNEL staining is also performed to identify apoptosis in neural cells. Treatment with SCF and G-CSF, alone or in combination, may act to decrease TUNEL staining (decrease apoptosis) in brain cells.

Example 9

Neuroprotective Effect(s) of SCF and G-CSF on Cortical Neurons In Vitro

To determine if SCF, alone or in combination with G-CSF, can protect neurons from excitotoxic damage, a neurotoxicity assay is performed in vitro.

In this assay, a primary culture of cortical neurons from embryonic d18 (E18) Sprague-Dawley (SD) rats is seeded on poly-D-lysine (PDL)-coated cover slips in a 24-well culture dish with ~0.8-1.0×10$^5$ cells/well. SCF and G-CSF (at concentrations of both 10 ng/ml and 20 ng/ml) are added to the culture medium 30 min after glutamate treatment (100 μm, overnight at 37° C.). For assessment of neurotoxicity, cortical neurons are incubated with calcein-AM (0.16 μM) for detecting live cells and ethidium homodimer (0.36 μM) for detecting dead cells in Hanks Buffered Salt Solution (HBSS, 1×) for 40 min at room temperature. Neurotoxicity is calculated as the percentage survival compared to control. Treatment with SCF, alone or in combination with G-CSF, may act to increase survival of cortical neurons.

Example 10

Effects of SCF and G-CSF in Promoting Brain or Neuronal Plasticity In Vitro and In Vivo To determine whether SCF and G-CSF, alone or in combination, can promote brain or neuronal plasticity, an in vitro cell culture study and a brain slice study were designed.

In an in vitro study, primary cortical neurons are seeded on PDL-coated cover slips in a 24-well culture dish with ~0.8-1.0×10$^5$ cells/well. Cells are grown in neural basal medium with N2 supplement (a commercial liquid containing chemicals which support neuron growth) for approximately 10-14 days and then treated with varying concentrations of SCF and G-CSF, alone or in combination, for approximately 3-7 days. After rinsing the cells with PBS, the cells are fixed with formaldehyde (4%) and incubated overnight. Primary antibodies, such as NF-200 and MAP2 (for identifying neurons), and synaptophysin and synapsin (for detecting synapses), are incubated with the fixed cells at 4° C. overnight. Fluorescent dye conjugated secondary antibodies are incubated at room temperature in the dark for 2 h and cells are examined using fluorescent microscopy for immunoreactivity. NF-200 and MAP immunostaining allows one to determine if cytokine treatment increased the branching of neuritis and/or dendrites. Synaptophysin and synapsin immunostaining allows one to determine if cytokine treatment increased the number of synapses.

In an in vivo brain slice study, executed to determine if SCF and G-CSF, alone or in combination, can increase neuronal transmission and the strength of the neuronal synapse, brains slices are treated with SCF and G-CSF, alone or in combination. Excitatory post-synaptic transmission, inhibitory post-synaptic transmission, and long-term potentiation of the synapses are recorded. Cytokine treatment, alone or in combination, is expected to increase excitatory post-synaptic transmission and long-term potentiation, and decrease inhibitory post-synaptic transmission.

Example 11

Role of SCF and G-CSF in Promoting Brain Self Repair: Neural Progenitor Cell Proliferation and Differentiation SCF receptor, c-Kit, and G-CSF receptor were found in the ventricular wall and subventricular zone of the brain. Therefore, experiments were designed to determine if SCF and G-CSF, alone or in combination, increase neural progenitor cell proliferation and differentiation. Two experiments were designed to test this hypothesis.

In an in vitro study, neural progenitor cells are dissected from the ventricular zone of E18 Sprague-Dawley rats. The neurospheres, neural progenitor cells, are treated with SCF, G-CSF, and SCF+G-CSF (100 ng/ml). The ability for self-renewal (determined by continual passage of the cell line) and multipotent differentiation are tested. After treatment with trypsin, single-celled neurospheres are plated on PDL-coated cover slips, and cells are grown in neural differentiation medium for a couple of days. Thereafter, the cells are processed for immunohistochemistry to identify neurons (using anti-βIII tubulin antibody), astrocytes (using an anti-GFAP antibody), and oligodendrocytes (using an anti-O4 antibody). Neural cell proliferation and differentiation are recorded over time in various cell passages.

In an in vivo study, 36 rats are randomly divided into five groups: sham control (n=4), PBS control (n=8), SCF (n=8), G-CSF (n=8) and SCF+G-CSF (n=8). Three hours after brain ischemia, induced by MCAO, the animals are treated with daily subcutaneous injections of cytokines (SCF: at 200 μg/kg and G-CSF: at 50 μg/kg) and intraperitoneal injections of BrdU (50 mg/kg), a cell-dividing marker, for seven consecutive days. Half of the animals from each group are sacrificed at day 8 for analysis of neural progenitor cell proliferation. The remaining half of the rats is killed at 28 d after the last day injection of BrdU (BrdU is administered for 7 days after focal brain ischemia), or 35 days after the induction of brain ischemia. Cell proliferation is accessed by immunohistochemistry using a mouse antibody for BrdU. Cell differentiation is determined by a double immunohistochemistry technique in which cells immunopositive for BrdU (a marker for cell division/proliferation) and NeuN (a marker for new neurons) are counted. Cells immunopositive for GFAP or S-100-p (markers for detecting new astrocytes) are also counted. Neural cell proliferation and differentiation are compared between the two groups.

Treatment with SCF and G-CSF, alone or in combination, may act to promote neural progenitor cell proliferation and differentiation.

Example 12

Role of SCF and G-CSF in Promoting Bone Marrow Stem Cell (BMSC) Differentiation into Neuronal Cells SCF and G-CSF have been implicated in the process of stimulating bone marrow stem cell proliferation. Previous studies have shown that neural cells may be recruited from blood cells. To test if the functional benefits of SCF and G-CSF are due to their stimulation of the differentiation of bone marrow stem cells into neural cells in the brain, an in vivo study was designed.

Mice (non-green and non-blue), of the same genetic background as green mice (containing cells labeled with green fluorescent protein) or blue mice (containing cells labeled with LacZ), are exposed to a half-lethal dose of X-ray irradiation to damage the bone marrow. Thereafter, irradiated animals receive a bone marrow transplantation from bone marrow harvested from green or blue mice. Approximately 4-8 weeks after bone marrow transplantation, grafted mice are subjected to cortical brain ischemia induced by MCAO surgery. SCF and G-CSF, alone or in combination, are administered 3 h after brain ischemia, and continued for seven days. The animals are sacrificed at selected time intervals (at 3 d, 7 d, 4 weeks, and 8 weeks after the cytokine injection). Blood-sourced neurons and glial cells are then identified as green cells or blue cells. For further identification of green or blue cells, brain sections are processed for immunohistochemistry to examine co-expression of neuronal markers (NeuN and NF200), astrocyte markers (GFAP and S-100), and a microglia marker (CD11b). Increased areas of neurogenesis are seen in animals treated with cytokines in the area of the brain surrounding the infarct, especially in the peri-infarct area.

Example 13

Functional Neuronal Network in the Brain After Treatment with SCF and G-CSF

If the functional benefits of SCF and G-CSF, alone or in combination, are due to their facilitation of brain or neuronal plasticity, brain self-repair can occur by endogenous neural stem cells or new neural cells recruited from the blood stream. Functional neuronal circuits may then result, serving as the anatomical basis for functional recovery.

To determine if SCF and G-CSF can restore a functional neuronal network in the brain, rats are treated with SCF and G-CSF, alone or in combination, after experimental brain ischemia, and are subjected to functional magnetic resonance imaging (fMRI). Functional MRI records changes in functional signals, whereas anatomical images record anatomical changes (e.g. neuron density) between the treated and control animals. On the day of the experiment, rats are anesthetized with isoflurane (4% induction and 2% maintenance via mask). Catheters are inserted into the femoral artery and vein to measure blood pressure and heart rate and for anesthetic delivery, respectively. After surgical insertion of catheters, rats are placed in the animal cradle and their heads are secured in a radio frequency (RF) coil. A heated water blanket is used to maintain body temperature during the fMRI experiments. Anesthesia is then switched to α-chloralose (60 mg/kg initially, followed by 25 mg/kg every 45 min, intraperitoneally) to allow detection of brain activity in the somatosensory cortex. Blood pressure and heart rate are recorded during the imaging experiments to assure the depth of anesthesia.

A forepaw stimulation experiment is then carried out, while the animal is under anesthesia, to determine how cytokine treatment affects functional neural recovery. To perform this experiment, a pair of needle electrodes are inserted subcutaneously in each forepaw under isoflurane anesthesia prior to switching to α-chloralose. The stimulation parameters, based on those reported in the literature, are as follows: 1.5 mA current intensity, 3 Hz frequency and pulse duration of 0.3 ms. The forepaw stimulation paradigm will consist of three stimulation periods of 18 sec and a resting period of 5 min. Functional MRI are acquired before, during, and after the stimulus to determine if there are any signal changes during the process. Anatomical images are also acquired prior to the forepaw stimulation paradigm.

Rats undergoing cytokine treatment may exhibit an increased signal in the cortex and in some subcortical areas compared to untreated controls, thus indicating that cytokine treatment facilitates functional neuronal signaling.

Example 14

Effect of SCF and G-CSF in the Treatment of Parkinson's Disease

To test the effect of SCF or G-CSF, alone or in combination, on neurological repair of the brain, a rat model of Parkinson's Disease (Duan et al., *Neuroscience* 57:261-174, 1993) is subjected to a unilateral 6-hydroxydopamine (6-OHDA) lesion in the brain and cytokine treatment.

Briefly, animals are injected with 6-OHDA into the brain, while under anesthesia (see Duan, supra). At various time points after the 6-OHDA lesion is made in the brain, animals are treated with the SCF or G-CSF, alone or in combination. Brains are examined after cytokine treatment to determine the effect of the treatment on dopamine production and neurological repair or regeneration in the region of the dopamine depleted striatum. Animals are examined for the effect of treatment on sensorimotor skills and coordination. A variety of sensorimotor tests are performed by one of skill in the art to determine the effectiveness of cytokine treatment in the rat model.

Treatment with SCF or G-CSF, alone or in combination, induces the recruitment of stem cells to the brain and prevents or reduces neurological degeneration. This recruitment of new stem cells to the brain participates in the formation of new dopamine-producing cells. Such method of treating a rat model of Parkinson's Disease with SCF or G-CSF, alone or in combination, is an important clinical tool for human therapy of Parkinson's Disease and other neurodegenerative disorders.

Example 15

Effect of SCF and G-CSF in the Treatment of Alzheimer's Disease

To test the effect of SCF or G-CSF, alone or in combination, on neurological repair of the brain, a mouse model of Alzheimer's Disease [transgenic mice overexpressing mutant forms of human β-amyloid precursor protein (APP)] are treated with the above-referenced cytokines and brains are examined after treatment for neurological repair or regeneration, or a decrease in the number of amyloid plaques.

Treatment with SCF or G-CSF, alone or in combination, induces the recruitment of stem cells to the brain and prevents or reduces neurological degeneration. This recruitment of new stem cells to the brain participates in controlling the formation of amyloid plaques, reducing neurotoxicity, and generally mediating the pathology associated with β-amyloid production. Such method of treating a mouse model of Alzheimer's Disease with SCF or G-CSF, alone or in combination, may prove to be an important clinical tool for human therapy of Alzheimer's Disease and other neurodegenerative disorders.

While the present invention has been described in terms of preferred embodiments, it is understood that variations and modifications will occur to those skilled in the art. Therefore, it is intended that the appended claims cover all such equivalent variations which come within the scope of the invention as claimed.

We claim:

1. A method of improving sensorimotor function in a mammal that has suffered a cerebral ischemia event, the method comprising administering a composition comprising granulocyte colony stimulating factor (G-CSF) polypeptide, alone or in combination with stem cell factor (SCF) polypeptide, in an amount effective to improve sensorimotor function, wherein the composition is administered during the chronic stage of stroke, wherein the composition has not been administered prior to three months after the cerebral ischemia event.

2. The method of claim 1, wherein the mammal is in need of improving its sensorimotor function 14 weeks after the cerebral ischemia event.

3. The method of claim 2, wherein the composition has not been administered to the mammal prior to 14 weeks after the cerebral ischemia event.

4. The method of any one of claims 1-3, wherein the mammal's sensorimotor function is assessed subsequently to administering the composition.

5. The method of any one of claims 1-3, wherein the mammal is a human.

\* \* \* \* \*